US012109103B2

(12) United States Patent
Ganz et al.

(10) Patent No.: US 12,109,103 B2
(45) Date of Patent: Oct. 8, 2024

(54) METHODS AND DEVICES FOR TREATING SPHINCTER DISORDERS

(71) Applicant: ESCHARA MEDICAL, LLC, Minnetonka, MN (US)

(72) Inventors: Robert A. Ganz, Minnetonka, MN (US); Gabriel L. Ganz, Minnetonka, MN (US); Ryan Timothy Balko, Rogers, MN (US); Justin James Herbert, Osseo, MN (US); Brett Allyn Williams, North Oaks, MN (US)

(73) Assignee: ESCHARA MEDICAL, LLC, Minnetonka, MN (US)

(*) Notice: Subject to any disclaimer, the term of this patent is extended or adjusted under 35 U.S.C. 154(b) by 0 days.

(21) Appl. No.: 18/404,655

(22) Filed: Jan. 4, 2024

(65) Prior Publication Data

US 2024/0138971 A1 May 2, 2024

Related U.S. Application Data

(63) Continuation of application No. 17/652,628, filed on Feb. 25, 2022, which is a continuation of application No. PCT/US2020/047831, filed on Aug. 25, 2020.

(60) Provisional application No. 62/891,803, filed on Aug. 26, 2019, provisional application No. 62/895,306, filed on Sep. 3, 2019, provisional application No. 62/932,260, filed on Nov. 7, 2019, provisional application No. 62/978,083, filed on Feb. 18, 2020.

(51) Int. Cl.
A61F 2/04 (2013.01)

(52) U.S. Cl.
CPC .......... *A61F 2/04* (2013.01); *A61F 2002/044* (2013.01); *A61F 2210/0004* (2013.01)

(58) Field of Classification Search
CPC ................. A61F 2/04; A61F 2002/044; A61F 2210/0004
See application file for complete search history.

(56) References Cited

U.S. PATENT DOCUMENTS

| | | | |
|---|---|---|---|
| 7,758,635 B2 * | 7/2010 | Parsonage | A61F 2/91 623/2.1 |
| 10,912,862 B2 * | 2/2021 | Mauney | A61L 27/227 |
| 11,033,375 B2 | 6/2021 | St. Germain | |
| 2005/0113904 A1 * | 5/2005 | Shank | A61F 2/86 623/1.38 |
| 2011/0015684 A1 * | 1/2011 | Belcheva | A61B 17/864 606/314 |
| 2020/0113570 A1 | 4/2020 | Jacobs | |
| 2020/0121441 A1 * | 4/2020 | Taylor | A61L 31/148 |
| 2020/0188080 A1 * | 6/2020 | Fiebig | A61B 17/12099 |
| 2022/0000599 A1 * | 1/2022 | St. Germain | A61M 25/003 |

(Continued)

*Primary Examiner* — Jerrah Edwards
*Assistant Examiner* — Aren Patel
(74) *Attorney, Agent, or Firm* — Gallium Law; Wesley Schwie; Justin Schwechter

(57) ABSTRACT

Devices and methods for treatment of bodily lumens and sphincters are disclosed. Some embodiments include methods and devices for inducing an inflammatory response and development of fibrosis, collagen, and/or scar tissue. In some embodiments, scaffolds may be composed of a matrix of filaments. Application of the methods and devices disclosed herein to treat Gastroesophageal Reflux Disease (GERD) and other sphincter disorders are discussed. Biodegradable scaffolds configured to induce an inflammatory response are also disclosed.

20 Claims, 10 Drawing Sheets

(56) References Cited

U.S. PATENT DOCUMENTS

2022/0257362 A1\* 8/2022 Nakayama ................ A61F 2/07
2022/0339324 A1\* 10/2022 Koul .................... A61L 27/222

\* cited by examiner

METHODS AND DEVICES FOR TREATING SPHINCTER DISORDERS

RELATED CASES

This application is a continuation of PCT Application No. PCT/US2020/047831, filed on Aug. 25, 2020 a titled, "Methods and Devices for Treating Sphincter Disorders," which, in turn, claims priority to the following applications: U.S. Provisional Application No. 62/891,803, filed on Aug. 26, 2019 and titled, "Method and Device to treat Gastroesophageal Reflux Disease (GERD) and other Sphincter Disorders"; U.S. Provisional Application No. 62/895,306, filed on Sep. 3, 2019 and titled, "Method and Device to treat Gastroesophageal Reflux Disease (GERD) and other Sphincter Disorders"; U.S. Provisional Application No. 62/932,260, filed on Nov. 7, 2019 and titled, "Method and Device to treat Gastroesophageal Reflux Disease (GERD) and other Sphincter Disorders"; and U.S. Provisional Application No. 62/978,083, filed on Feb. 18, 2020 and titled, "Method and Device to treat Gastroesophageal Reflux Disease (GERD) and other Sphincter Disorders." Each priority application listed above is hereby incorporated by reference in its entirety.

TECHNICAL FIELD

The present disclosure relates generally to the field of implantable medical devices and associated methods. More particularly, some embodiments relate to biodegradable implantable devices and methods for reinforcement of a sphincter, such as the lower esophageal sphincter (LES), including devices and methods for reinforcing a sphincter through inducing a biologic response to an implantable device.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1A:
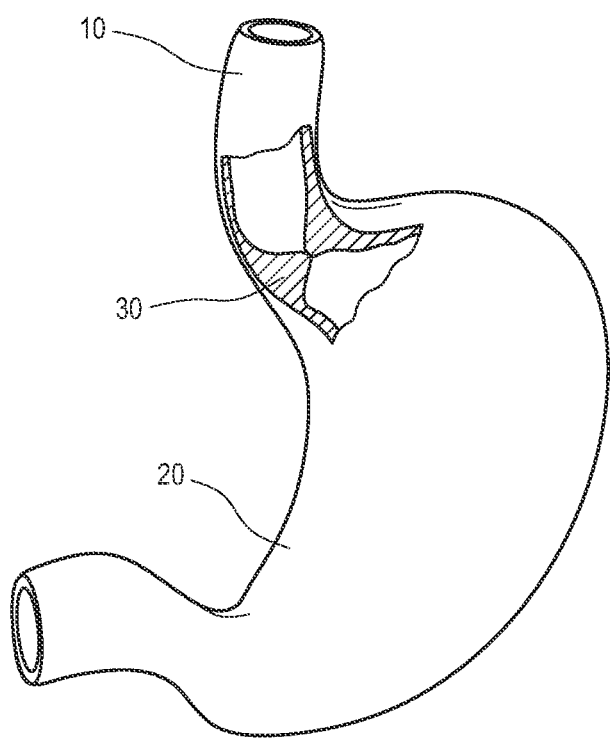
FIG. 1A is an illustration of a portion of an esophagus and stomach of a patient and the lower esophageal sphincter (LES) between the stomach and esophagus.

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic interaction. Two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., an adhesive). The phrase "fluid communication" is used in its ordinary sense, and is broad enough to refer to arrangements in which a fluid (e.g., a gas or a liquid) can flow from one element to another element when the elements are in fluid communication with each other.

As used herein, "biodegradable" and "bioabsorbable" are used to describe materials that break down when implanted in the body. Examples of biodegradable and/or bioabsorbable materials include suture materials that are molecularly broken down when implanted in the body. Materials within the scope of this definition include materials that break down within a few days of implantation as well as materials that break down over a time period of days to years, including materials that break down in the body over several days, materials that break down in the body over several weeks, materials break down in the body over several months, and materials that break down in the body over years.

As used herein, a "tissue collar" refers to any tissue genesis, neogenesis, growth, or thickening induced by an inflammatory response to the introduction of a bioabsorbable material, including tissue growth comprising an acute and/or chronic cellular response, foreign body reaction, granuloma formation, giant cell formation, fibrosis, collagen, and/or scar tissue.

Placement of a foreign material within the human body generally results in an inflammatory response to the foreign body. This response can be characterized as an initial acute inflammation (neutrophils), followed by chronic inflammation (monocytes, lymphocytes), then granuloma formation/granulation tissue, followed by giant foreign body cell formation, and finally the formation of fibrosis, collagen, and/or scar tissue. Treatments within the scope of this disclosure include the deliberate inducement of an inflammatory response, and the formation of the fibrosis, collagen, and/or scar tissue that follows to support or reinforce a sphincter.

Sphincters are rings of muscle tissue that surround lumens, passages, openings, and/or portions of organs within the body. Sphincters in a human body are typically tonically contracted, and such contraction of a sphincter may close or narrow the sphincter in order to control passage of gas, fluids, food, stool, urine, or other materials through the sphincter, in either direction (for example oral or aboral with reference to the esophagus). In some instances, a sphincter may lose the ability to close off or control material passage. For example, a sphincter may be stretched, be injured or deteriorate with age and thus lose efficacy, or the ability to control material passage through the sphincter.

The esophagus extends along the gastrointestinal tract to the upper portion of the stomach. The lower esophageal sphincter (LES) is a sphincter disposed between the esophagus and the stomach and controls flow between those two organs. The gastroesophageal junction (GEJ) refers to the area or zone of transition between the esophagus and the stomach. The GEJ can be understood as including a small distal portion of the esophagus, a small proximal portion of the stomach, and the transition area between these portions. The LES is disposed in the region of the GEJ.

The LES is one example of a sphincter that may lose efficacy in humans. For example, the LES may fail to close, or only be able to close partially, or the sphincter may close but be too easily opened when subjected to increased gastric volume or increased gastric or intra-abdominal pressure.

Gastroesophageal reflux disease (GERD) refers to pathologic reflux or regurgitation of gastric content into the esophagus from the stomach. Gastric content refers to materials present in the stomach such as acid, bile, pepsin, pancreatic enzymes, partially digested food, and so forth. GERD may result from failure of the LES in closing off the opening between the esophagus and the stomach, i.e., the sphincter can be lax, hypotensive or patulous, or the LES can close but can be forced open too easily by excess gastric volume or pressure or increased intra-abdominal pressure. While small amounts of reflux occur in healthy individuals, GERD refers to conditions where the refluxed material is large enough or frequent enough to cause damage to the esophagus, cause heartburn, regurgitation, other chest discomfort, or other symptoms. Damage to the esophagus may be associated with conditions such as reflux esophagitis, Barrett's esophagus, esophageal stricture, ulceration, and bleeding, for example, while other symptoms of GERD include heartburn, regurgitation, and chest discomfort. Various factors including age, stress to the LES from overeating, obesity, trauma, and various anatomical changes such as hiatal hernia, may lead to shortening of the overall sphincter length, or intra-abdominal LES length, or loss of sphincter pressure, leading to sphincter dysfunction and subsequent GERD. The sphincter can weaken or fail because it is too weak or too short to maintain adequate closure, or the sphincter becomes excessively compliant and can be forced open too easily.

GERD is a common condition affecting various populations. In the United States, there are at least 60 million individuals with GERD with at least 20 million cases severe enough to require daily treatment by medication. Treatments for GERD include lifestyle changes such as weight loss and elevation of the head of the bed, and medications, including anti-acids or antisecretory medications, and anti-reflux surgery or anti-reflux endoscopic techniques.

Medications for treatment of GERD include antisecretory medications such as H2 receptor antagonists (Tagamet and Zantac, etc.) as well as proton pump inhibitors (PPIs) such as Prilosec and Nexium, etc. H2 receptor antagonists and PPIs partially or completely block gastric acid secretion, helping to improve GERD symptoms and facilitate healing of esophagitis. However, antisecretory medications fail to control symptoms at least 30% of the time, are expensive, do not address the reflux pathophysiology, and can be associated with side effects such as vitamin and mineral malabsorption, kidney disease, osteoporosis, increased diarrhea, etc.

Surgical and endoscope treatments for GERD include permanently positioning the proximal portion of the stomach around the LES (i.e., Nissen fundoplication), or implantation of permanent materials or devices configured to augment, support, or extend the effective length of the LES, and/or augment the sphincter to decrease compliance (e.g., LINX magnetic augmentation). These techniques can be effective in treating the symptoms of GERD and can help address GERD pathophysiology, however they are frequently associated with side effects related to the permanent nature of the implanted materials, including dysphagia, gas-bloat syndrome, vagal nerve damage, and device migration.

Methods of treatment within the scope of this disclosure include methods of inducing an inflammatory response and/or inducing the formation of a tissue collar adjacent a sphincter location, to reinforce the sphincter or otherwise favorably affect sphincter mechanics. Tissue collars adjacent may be adjacent to the sphincter in various patterns (such as circumferential, hemi circumferential, piecemeal, and so forth) including embodiments wherein the tissue collar is adjacent and/or around a body lumen or organ that includes the sphincter. The tissue collar may be adjacent the sphincter in a position where the tissue collar is external to the sphincter and/or external to lumen or organ tissue around the sphincter. Embodiments of bioabsorbable devices configured to induce such an inflammatory and/or tissue response are also within the scope of this disclosure. Methods of treatment wherein a bioabsorbable device is completely bioabsorbed and only a tissue cuff remains to reinforce a sphincter, as well as methods where a portion of an otherwise bioabsorbable device remains adjacent the sphincter along with the tissue cuff are within the scope of this disclosure. One of ordinary skill in the art, having the benefit of this disclosure, will recognize that a variety of structures and devices may be designed and configured to induce a desired inflammatory and/or tissue response and the present disclosure is not limited to the specifically disclosed examples of implantable devices.

In some embodiments, the present disclosure relates to devices and methods for introducing a bioabsorbable material into the body to stimulate an inflammatory response and/or tissue growth adjacent a sphincter. The bioabsorbable material may be adjacent to the sphincter in various patterns (such as circumferential, hemi circumferential, piecemeal, and so forth) including embodiments wherein the bioabsorbable material adjacent and/or around a body lumen or organ that includes the sphincter. The bioabsorbable material may be adjacent the sphincter in a position where the bioabsorbable material is external to the sphincter and/or external to lumen or organ tissue around the sphincter, including instances wherein there is a gap between the biobsorbable material and a wall of lumen or organ containing the sphincter. In some embodiments, a bioabsorbable material introduced adjacent to, and/or around the wall of a body lumen or organ adjacent a sphincter will induce a biologic response around said wall of the body lumen as the material bioabsorbs. This biologic response may, in turn, result in development of acute inflammation, chronic inflammation, granuloma formation, foreign body giant cell formation, fibrosis, collagen, and/or scar tissue at the treatment site. In other words, the bioabsorbable material may induce formation of a tissue collar. This tissue may tend to stabilize and reinforce the lumen wall adjacent the sphincter, decreasing wall compliance, increasing functional sphincter length, and augmenting sphincter performance at the sphincter site and restoring sphincter functionality. Devices wherein a bioabsorbable device is completely bioabsorbed and only a tissue cuff remains to reinforce a sphincter, as well as methods where a portion of an otherwise bioabsorbable device remains adjacent the sphincter along with the tissue cuff are within the scope of this disclosure.

As compared to implantation of permanent devices into a patient, use of bioabsorbable materials reduces or eliminates adverse issues and side effects related to permanent devices such as infection, migration, dysphagia, gas-bloat syndrome, vagal nerve damage, etc.

Though certain specific applications, such as treatment of the LES, may be described herein, application and adaptation of the devices and methods discussed herein to any sphincter is within the scope of this disclosure. Discussion of specific examples does not limit the application of these concepts to those examples.

In some embodiments the present disclosure includes implantation of a bioabsorbable scaffold around a portion of the esophagus, stomach, and GEJ in the region of the LES. Development of fibrosis, collagen, and/or scar tissue adjacent to, and/or around, the esophageal wall may tend to reinforce the esophageal wall adjacent the LES and, in turn, augment, stabilize and restore functionality to the LES.

As further detailed herein, devices and methods within the scope of this disclosure may induce a tissue response in a variety of ways using a variety of bioabsorbable materials. It is within the scope of this disclosure to modify parameters such as surface area of a bioabsorbable implant, rate of bioabsorption (including use of multiple materials with different bioabsorption rates), porosity of the implant, shape of the implant, height and width of the implant, location of the introduction of the bioabsorbable material, pattern of introduction of the bioabsorbable material, tensile strength of the materials implanted, and so forth to affect the treatment.

FIG. 1A is an illustration of a portion of an esophagus 10 and a stomach 20 of a patient. A lower esophageal sphincter (LES) 30 is also shown in a partial cutaway view. As shown in FIG. 1A, the LES 30 is in a baseline, closed state. In this position, the LES 30 reduces or prevents reflux of the contents of the stomach 20 into the esophagus 10. In healthy individuals, the LES 30 is further configured to intermittently relax and open to allow passage of food from the esophagus 10 into the stomach 20 while limiting reflux.

As noted above, age, persistent overeating with stretching of the LES, obesity and other conditions can effectively decrease sphincter pressure or loosen and/or shorten the LES 30. In such instances, the ability of the LES 30 to limit reflux may be compromised, resulting in excess reflux or regurgitation of stomach contents into the esophagus 10 and, potentially, result in GERD.

Figure 1B:
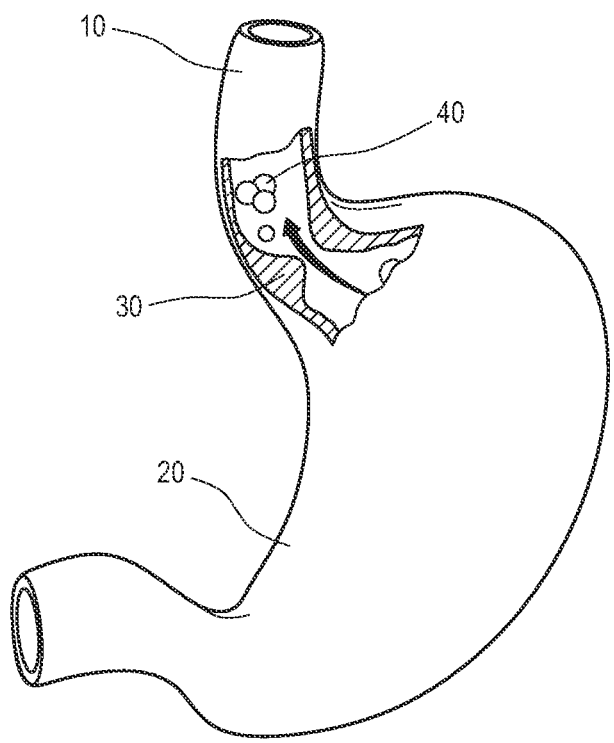
FIG. 1B is an illustration of the portion of the esophagus and stomach of FIG. 1A, illustrating gastric reflux through the LES.

FIG. 1B is an illustration of the portion of the esophagus 10 and the stomach 20 of FIG. 1A. As compared to FIG. 1A, however, in FIG. 1B, the LES 30 is partially open, allowing reflux material 40 to travel from the stomach 20 to the esophagus 10. Thus, in patients where the LES 30 frequently or permanently fails to fully close, and/or can be more easily forced open, said gastric reflux may lead to GERD and other conditions.

Introduction of a foreign material within the human body will provoke an inflammatory response as described above, whether the foreign material is permanent or bioabsorbable. Additionally, foreign material breaking down and being absorbed by the body will further invoke an inflammatory response. As bioabsorbable foreign material is broken down within the human body, among other substances, lactic acid can build up in the area around the bioabsorbed material, which induces a local decrease in pH, and an additional inflammatory response. In other words, the inflammatory response to a bioabsorbable material is driven by both the physical presence of the material itself (and the body's reaction thereto) and chemical changes that result as the material is broken down during bioabsorbtion, which also can trigger an additional response.

Accordingly, as detailed herein, the inflammatory response to devices within the scope of this disclosure may vary over time. For example, a device may be comprised of two or more materials with different rates of bioabsorbtion, including materials that bioabsorb relatively rapidly at first resulting in a "burst" of bioabsorbtion, and thus a burst of inflammatory response, then followed by a material with relatively slower bioabsorption and a more delayed inflammatory response. A single device may be comprised of two, three, four, or more materials, each configured to invoke a burst of inflammatory response at different times. Materials with different expected rates or time periods of bioabsorption may be used to create devices within the scope of this disclosure.

Figure 2A:
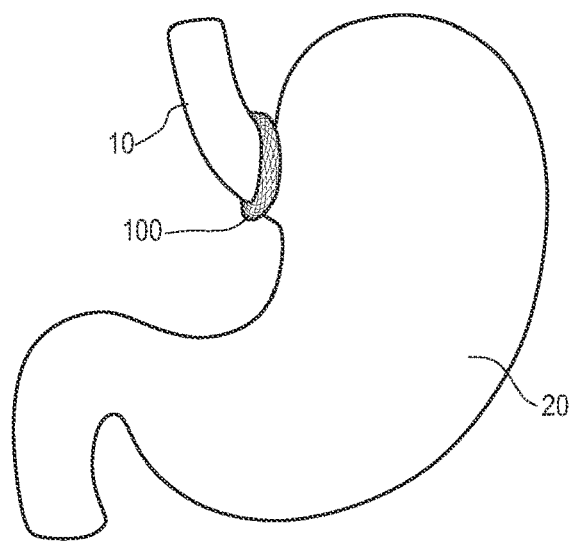
FIG. 2A illustrates a biodegradable scaffold around a portion of an esophagus, stomach, and LES.

FIG. 2A illustrates a bioabsorbable scaffold 100 around a portion of an esophagus 10 at the gastroesophageal junction (GEJ), in the region of the LES, between the esophagus 10 and the stomach 20. As noted above, introduction of a foreign material, such as the scaffold 100, induces an inflammatory response around the tissue of the wall of the esophagus 10.

Figure 2B:
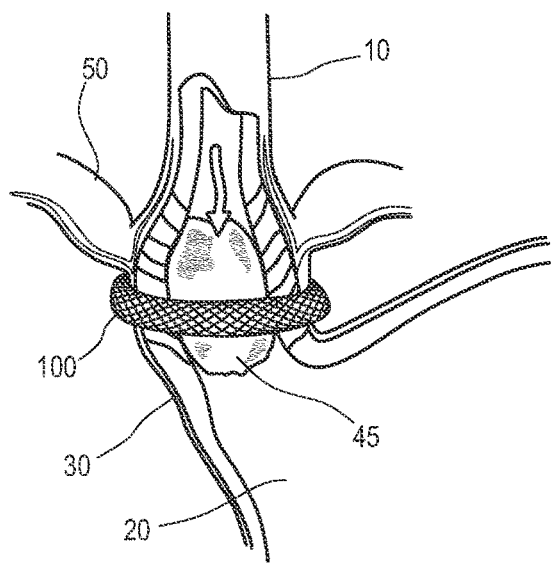
FIG. 2B is a cross sectional view of a portion of the esophagus, stomach, and LES of FIG. 2A depicting sphincter and scaffold function during swallowing of a food bolus (note the scaffold is not in cross section).

FIG. 2B is a cross sectional view of a portion of the esophagus 10 of FIG. 2A. FIG. 2B also illustrates the scaffold 100 disposed around the wall of the esophagus 10, at the GEJ and in the region of the LES 30. For clarity in illustration, the scaffold 100 is not shown in cross section. As noted above, the muscular LES 30 is within the GEJ between the stomach 20 and the esophagus 10. In the illustrated configuration, a bolus of food 45 is shown passing from the esophagus 10, through the LES 30, and into the stomach 20.

Figure 2C:
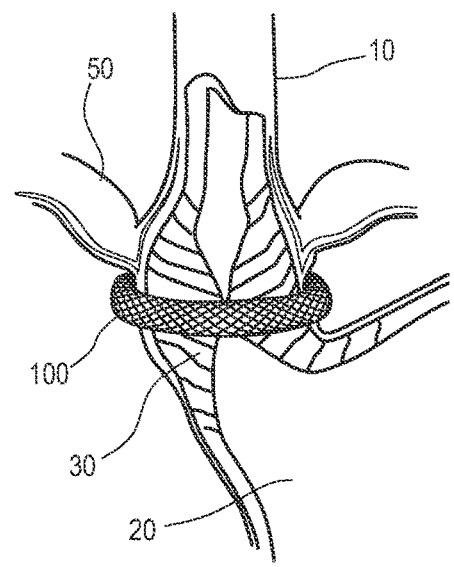
FIG. 2C is a cross sectional view of the portion of the esophagus and stomach of FIG. 2A with the LES in a different state than that of FIG. 2B depicting sphincter and biodegradable scaffold function in closed state (note the scaffold is not in cross section).

FIG. 2C is a cross sectional view of the portion of the esophagus 10 of FIG. 2A with the LES 30 in a closed state, as compared to the open state of FIG. 2B. For clarity in illustration, the scaffold 100 is not shown in cross section.

With reference to FIGS. 2A-2C, the scaffold 100 may be disposed around the esophagus 10 such that it approximates and/or is contiguous to the esophagus, but does not exert a compressive force on the esophagus 10 when the esophagus 10 and LES 30 are in a closed state. For example, the scaffold 100 may be sized such that when food is not disposed within the esophagus 10, the scaffold 100 is loosely disposed around the esophagus 10. The scaffold 100 may also be sized such that is it configured to match the size of the esophagus 10 in a relaxed state, that is, it does not compress the esophagus 10, but also has limited slack around the circumference of the esophagus 10. As shown in FIG. 2B, passage of food through the esophagus 10, the LES 30, and the scaffold 100 may tend to enlarge the esophagus 10, leading to a tighter interaction with the scaffold 100. In some embodiments, the scaffold 100 may be configured to flexibly expand and contract in such instances with the passage of food.

Embodiments wherein the scaffold 100 is more tightly coupled to the esophagus 10 are also within the scope of this disclosure. For instance, depending on the weakness of the LES 30 and the degree to which the LES 30 is excessively compliant or damaged, a practitioner may elect to more tightly constrain the GEJ to better support the LES 30. Thus, embodiments wherein the scaffold 100 is tightly coupled to the esophagus in the region of the GEJ and LES, embodiments wherein the scaffold 100 is loosely disposed around the esophagus in the region of the GEJ and LES, and embodiments wherein the scaffold 100 is configured to contact but not compress the esophagus in the region of the GEJ and LES are all within the scope of this disclosure. Furthermore, any such arrangement of the scaffold 100 with respect to the esophagus 10 may induce an inflammatory response. Treatments within the scope of this disclosure include reinforcing a sphincter only with scaffold-induced tissue growth, not necessarily requiring compressive or supportive pressure to be exerted by the scaffold 100.

As noted above, and further discussed below, the scaffold 100 may be comprised of a bioabsorbable material. As the bioabsorbable scaffold material breaks down, the scaffold 100 is ultimately completely bioabsorbed by the body and ultimately disappears completely, leading to a condition where only the tissue generated by the inflammatory response remains at the treatment location. The induced tissue growth, which can be understood as a tissue collar or collar of fibrosis, collagen, and/or scar tissue, may thus continue to reinforce the sphincter after the scaffold 100 is no longer present. As also noted above, a "tissue collar" as used herein refers to any tissue genesis, neogenesis, growth or thickening induced by an inflammatory response to the introduction of a bioabsorbable material, including tissue growth comprising fibrosis, collagen, and/or scar tissue.

Figure 2D:
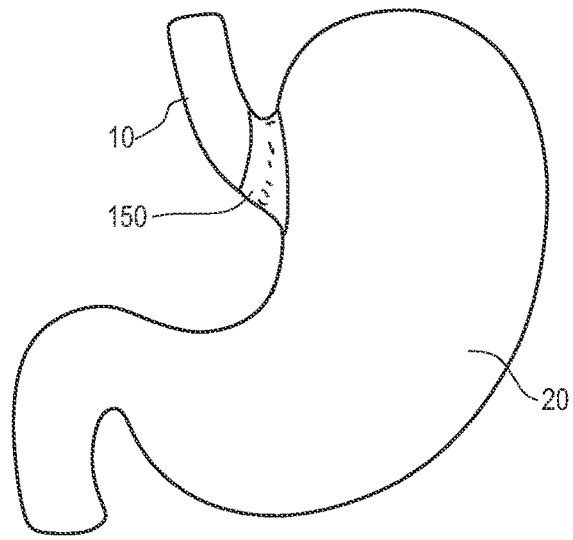
FIG. 2D illustrates the portion of the esophagus, stomach, and LES of FIG. 2A showing tissue growth in response to the scaffold of FIG. 2A after bioabsorption of the scaffold.

FIG. 2D depicts the portion of the esophagus 10 of FIG. 2A showing tissue growth as a tissue collar 150 in response to the scaffold 100 of FIG. 2A. Thus, FIG. 2D illustrates the state where the scaffold 100 of FIGS. 2A-2C has been completely broken down and absorbed by the body and only the tissue collar 150 remains to reinforce and support the LES 30.

The tissue collar 150 may augment and reinforce the wall of the esophagus 10, in the region of the GEJ/LES, augmenting the sphincter via increasing functional sphincter length and reducing compliance adjacent the LES 30. This, in turn, may make the LES 30 less likely to allow reflux, thus treating reflux symptoms and GERD and promoting healing of injuries to the esophagus 10 caused by the frequent presence of reflux material. The tissue collar 150 may be disposed adjacent to the outside surface of the esophagus 10 and thus may not constrict or narrow the lumen of the esophagus 10.

Treatments wherein a sphincter is treated by reinforcing the corresponding body organ and/or lumen along a length of the organ and/or lumen extending from a position along and also beyond the sphincter on one or both ends of the sphincter are also within the scope of this disclosure. In other words, treatments may be configured to induce the growth of a tissue collar (such as tissue collar 150) that begins at a location along a body organ or lumen along, proximal, and/or distal of the location of the sphincter along the body organ or lumen. Treatments configured to induce growth of a continuous tissue collar along the treatment length as well as treatments comprising discrete circumferential bands at two or more positions along the treatment length are likewise within the scope of this disclosure.

Figure 2E:
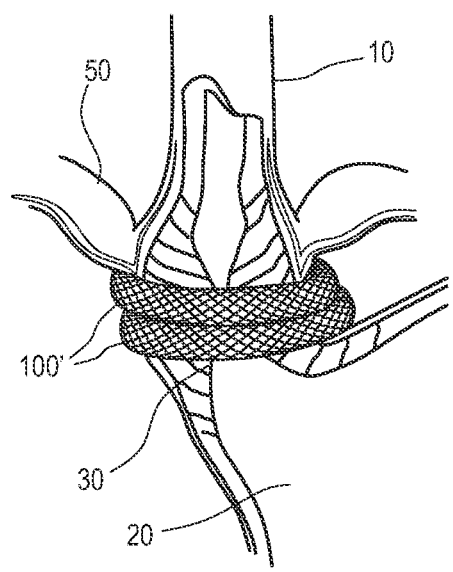
FIG. 2E is a cross sectional view of a portion of the esophagus, stomach, and LES of FIG. 2A with a scaffold disposed around the esophagus (note the scaffold is not in cross section).
Figure 2F:
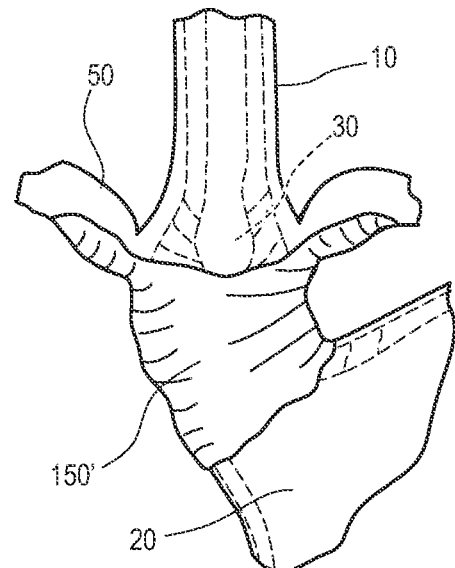
FIG. 2F is a portion of the esophagus, stomach, and LES of FIG. 2E showing tissue growth in response to the scaffold of FIG. 2E after bioabsorption of the scaffold.
Figure 2G:
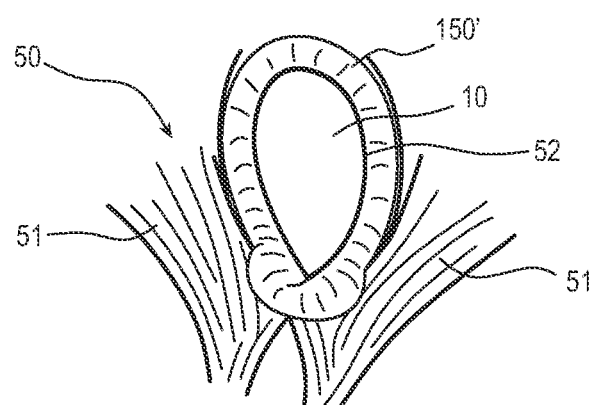
FIG. 2G is a view of the inferior aspect of the diaphragm, specifically the crus muscles and diaphragmatic hiatus, through which the esophagus exits, the esophagus and tissue growth of FIG. 2F.

Methods of treatment of organ wall, lumen and sphincter may thus comprise methods of inducing inflammation and/or the formation of a tissue collar to reinforce body organ, lumen or tissue along or adjacent the sphincter location. Additionally, in some embodiments, treatment methods may additionally or alternatively comprise inducing an inflammatory response and/or the formation of a tissue collar to anchor the organ itself and or the lumen to other body structures adjacent the organ or the lumen. In one potential example, referring back to FIGS. 2E-2G, treatment of the LES 30 may comprise anchoring the esophagus 10 to the diaphragm 50. FIG. 2E is a cross sectional view of a portion of the esophagus 10 with a scaffold 100' disposed around the esophagus 10 in two loops. For clarity in illustration, the scaffold 100' is not shown in cross section. FIG. 2F is a portion of the esophagus 10 showing tissue growth 150' in response to the scaffold 100' from FIG. 2E. FIG. 2G is an inferior view of the diaphragm and diaphragmatic crus muscles 51 and diaphragmatic hiatus 52 where the esophagus 10 passes through the diaphragm 50, and tissue growth 150' from the scaffold 100' of FIG. 2E. The stomach 20 and LES 30 are also shown in these figures. Though FIG. 2F illustrates a single tissue collar 150' formed from both loops of the scaffold 100', treatments where any number of scaffolds are spaced such as to form discrete tissue collar rings are likewise within the scope of this disclosure.

As shown FIGS. 2E to 2G, the esophagus 10 may pass through the diaphragm 50 near or adjacent the LES 30. Placement of the scaffold 100 may be configured to induce formation of a tissue collar that tends to couple the esophagus 10 and/or the stomach 20, and/or the GEJ to the diaphragm 50. For example, the scaffold 100 may be placed in contact with or in proximity to the diaphragm 50 as well as the esophagus 10 and/or the stomach 20. The induced tissue collar (150 of FIG. 2D) may extend between the esophagus 10 and/or the stomach 20 to the diaphragm 50, coupling the diaphragm 50 to the esophagus 10 to further reinforce the esophageal sphincter by keeping it in physiologic position within the diaphragmatic hiatus and/or distal to the diaphragm. By scarring the GEJ/LES in this position, the LES is buttressed by the diaphragm restoring sphincter competency.

Such a treatment may also comprise a treatment for a hiatal hernia, a condition where a portion of the stomach 20 extends proximally through a weakened portion of the diaphragm 50 (such as at or adjacent the diaphragmatic hiatus 52), i.e., an area where the diaphragmatic crus muscles have separated (see, for example, the view of FIG. 2G illustrating the relationship of the esophagus 10 and the crus muscles 51 of the diaphragm 50). Still further, methods and devices within the scope of this disclosure may be utilized to reinforce a hernia repair. For example, a practitioner may repair a hernia by approximating and suturing the crus muscles of the diaphragm 50 together, restoring the diaphragm to normal function. Oftentimes, especially in elderly patients there is a lack of collagen tissue in the region of the crus repair, and the repair will fall apart post-operatively. By adding a bioabsorbable scaffold in the region of the GEJ positioned to buttress the LES but also impact the underside of the diaphragm, a practitioner can add collagen and scar tissue to the crus muscles concurrently with reinforcing the LES; this then will also reinforce a hiatal hernia repair, often done in conjunction with anti-reflux surgery by inducing formation of a tissue collar in the region of the crus muscles between the diaphragm and esophagus to support the repair. Thus by positioning the bioabsorbable material in the region of the GEJ/LES and simultaneously on the underside of the diaphragm, in the region of the crus muscles, as the material bioabsorbs and collagen and scar tissue forms, the practitioner can augment the LES, and also aid the longevity of a hiatal hernia repair by helping anneal the crus muscles together, and can also scar the GEJ/LES in appropriate physiologic position relative to the diaphragmatic hiatus and/or below the diaphragm in the abdomen.

Various scaffold designs are within the scope of this disclosure. Scaffolds within the scope of this disclosure may comprise various weaves or webbing of filaments, including monofilaments and/or braided filaments, alone or in combination. Scaffolds may also comprise continuous materials, strips of porous materials, and so forth. Scaffolds may be configured to be applied as multiple wraps around a body lumen, such as wrapped helically around and along a longitudinal length of the lumen. Scaffolds may be configured with multiple layers and may be applied in multiple layers. Scaffolds within the scope of this disclosure may include markings denoting length along the longitudinal length of the scaffold.

Additionally, scaffolds within the scope of this disclosure may be comprised of multiple materials, including materials with different rates of bioabsorption. For example, a scaffold may comprise a matrix of filaments or fibers (such as a braid or lattice of filaments) where some filaments are made of a first material that bioabsorbs quickly and other filaments are made of a material that bioabsorbs more slowly. Scaffolds may also be comprised of three, four, five, or more materials with different bioabsorption rates and or different weave patterns or combinations of weave patterns, material of different porosities, etc.

Furthermore, the biodegradation or the bioabsorbable materials may tend to induce an inflammatory response, as the material breaks down and interacts with the body. In some embodiments a first material may be configured to provide a burst of inflammatory response as the material breaks down relatively quickly (for example over a period of a few days to several weeks) at a first time period and a second material may be configured to provide a second burst of inflammatory response as the material breaks down more slowly (for example over a period of months to years), defining a second, delayed time period. In some embodiments, a scaffold within the scope of this disclosure may be comprised of a first material that bioabsorbs over a period of 10 to 30 days, a second material that bioabsorbs over a period of 30 to 60 days, a third material that bioabsorbs over a period of 60 to 120 days, a fourth material that bioabsorbs over a period of 120 days to a year, and a fifth material that bioabsorbs over a period of time greater than one year. Any subset of such materials and any range of rates of bioabsorbtion, including the use of nonbioabsorbable materials in connection with bioabsorbable materials, is within the scope of this disclosure.

Materials may further be configured such that the material breaks down relatively slowly at first, then the rate of bioabsorbtion increases over time. For example, a material or filament may be coated with a material that bioabsorbs slowly, but have a core of material that bioabsorbs quickly. As the coating breaks down, the core may be exposed and deliver a burst of inflammatory response as the core bioabsorbs. Likewise, a material or filament may be coated with a material that bioabsorbs quickly, but have a core of material that bioabsorbs slowly. This may deliver a burst of inflammatory response upon initial implantation while providing a slower and lasting inflammatory response as the coating breaks down. Scaffolds with three, four, five, or more materials so configured are likewise within the scope of this disclosure. Still further, any combination of materials that bioabsorb at different rates and/or provide bursts of inflammatory responses at different time periods are within the scope of this disclosure.

As noted above, the material comprising the scaffold may affect the degree and timing of the inflammatory response. Additionally, the structure of the scaffold may affect the inflammatory response. For woven or braided scaffolds, for instance, the filament size, surface roughness, and filament spacing may all affect the inflammatory response. In some embodiments, scaffold filaments may comprise barbs, hooks, or other features along the length of the filament. For braided, woven, porous, and continuous scaffolds, surface area, surface roughness, porosity, weave and or fiber density, and overall shape may also affect the inflammatory response. In some embodiments, scaffolds with more surface area may interact with bodily tissues at more locations and thus induce a greater inflammatory response. Furthermore, scaffolds configured with greater surface area may tend to break down or bioabsorb more quickly, or cause more inflammation and tissue reaction, as more bioabsorbable material is exposed to the body. As noted above, higher rates of bioabsorbtion may induce higher rates of inflammatory response (such as related to the presence of lactic acid, or other acids and breakdown materials), thus scaffolds may be configured with more or varied surface area to induce a greater inflammatory response.

Various parameters of the scaffold may be adjusted to adjust the expected inflammatory response of a scaffold. In some embodiments, scaffolds comprised of woven or braided filaments may be tuned to adjust the expected inflammatory response of the scaffold. Again, such parameters may include filament size, tightness of the braid and/or density of the filaments, shape of the braided filaments (e.g., tubular, flat, layered), porosity of the weave, and so forth.

Figure 3A:
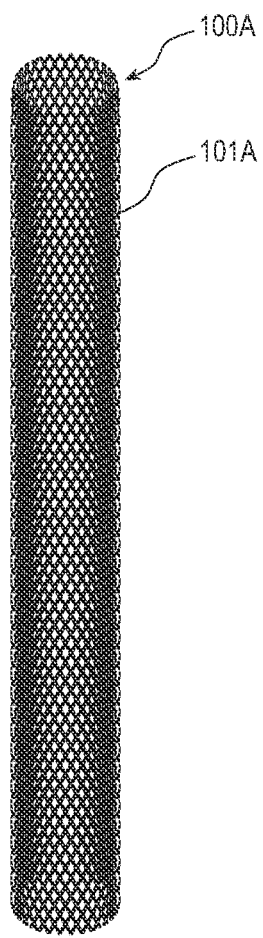
FIG. 3A illustrates one embodiment of a biodegradable tubular scaffold.
Figure 3B:
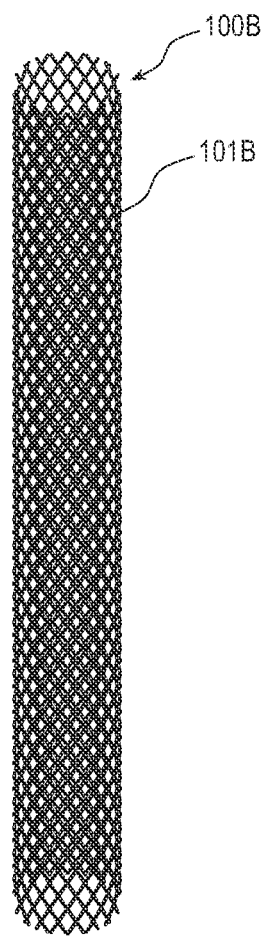
FIG. 3B illustrates another embodiment of a tubular scaffold.
Figure 3C:
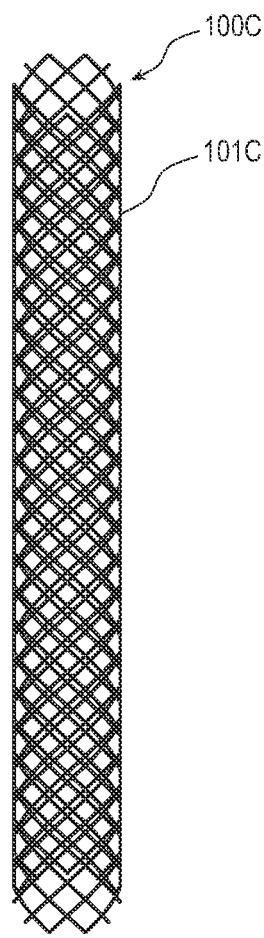
FIG. 3C illustrates another embodiment of a tubular scaffold.

In some embodiments, scaffolds within the scope of this disclosure may comprise tubular braids of filaments. FIG. 3A illustrates one embodiment of a tubular scaffold 100A comprising filaments 101A braided relatively tightly together. A relatively tight braid such as that of scaffold 100A may be understood as having a high filament density, meaning the number of filaments 101A disposed in a certain amount of area along the braid is high. FIG. 3B illustrates another embodiment of a tubular scaffold 100B comprising filaments 101B more loosely braided together as compared to the braid of scaffold 100A. FIG. 3C illustrates another embodiment of a tubular scaffold 100C comprising filaments 101C even more loosely braided together. The filament density of scaffolds 100B and 100C is thus lower than that of scaffold 100A.

Figure 3D:
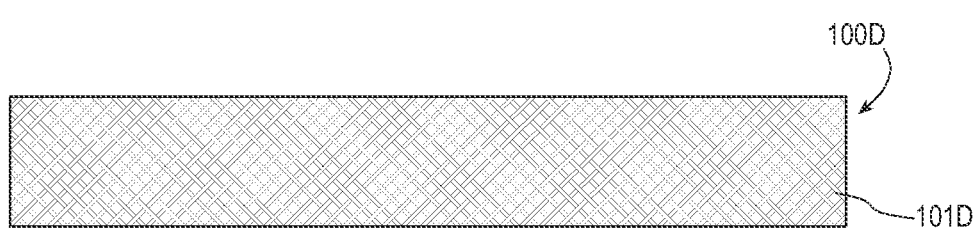
FIG. 3D illustrates an embodiment of a flat woven scaffold.

In addition to tubular braided scaffolds as shown in FIGS. 3A-3C, a variety of shapes and configurations of scaffolds are within the scope of this disclosure. FIG. 3D illustrates an embodiment of a flat woven scaffold 100D, for example. Flat scaffolds such as 100D may have a variety of filament densities, sizes, and heights and may be made of a single weave layer of filaments 101D, may be made of filaments 101D woven together in multiple layers to increase the thickness of the scaffold 100D, or may be comprised of singly woven layers stacked on each other.

Scaffolds within the scope of this disclosure may comprise multiple layers, including flat scaffolds with multiple sublayers (such as a scaffold formed by placing two or more scaffolds in the form of scaffold 100D on top of each other), tubular scaffolds disposed coaxially with each other, and so forth. The layers may be coupled or fixed to each other or may be configured as displaceable with respect to each other. Various layers may be comprised of different materials and may have different structures. For example, FIG. 3E shows a tubular scaffold comprised of the scaffold 100A of FIG. 3A and the scaffold 100B of FIG. 3B in a coaxial arrangement.

Figure 3E:
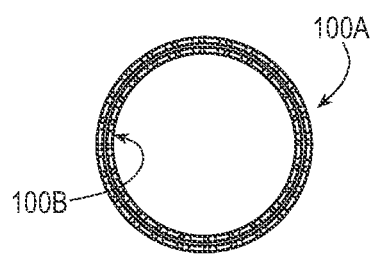
FIG. 3E illustrates the tubular scaffolds of FIGS. 3A and 3B disposed in a coaxial arrangement.

Scaffolds with multiple layers, whether arranged in a tube within a tube or coaxial arrangement such as shown in FIG. 3E, a multilayered flat scaffold, or any other shape may be configured with various material properties in each layer. In other words, each layer of a multilayered scaffold may comprise a different material from others and any layer can comprise any combination of materials (for example a braided layer of filaments of a plurality of materials). Multilayered scaffolds where one or more layers have the same properties are also within the scope of this disclosure.

Additionally or alternatively, tubular scaffold structures can be non-woven or non-braided, such as hollow tubular shapes defined by a wall of helically wound filaments, such as in the form of a hollow torque cable. The tubular shapes can also be completely solid, including solid forms made of filaments disposed directly adjacent each other, continuous solid materials such as extruded or molded polymers, three dimensional matrices of filaments that define cells and openings in the matrix but no central hollow section, and so forth. Scaffold shapes can also be combinations of tubular structures in various combinations with flat structures, or layers of flat inner or outer structures, combined with inner or outer tubular structures.

Figure 3F:
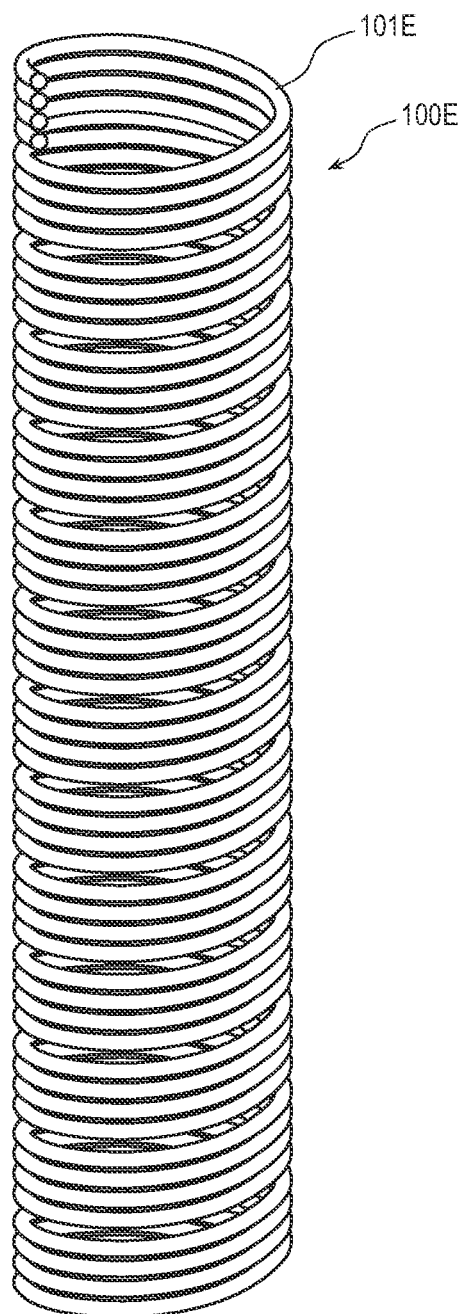
FIG. 3F illustrates another embodiment of a tubular scaffold.
Figure 3G:
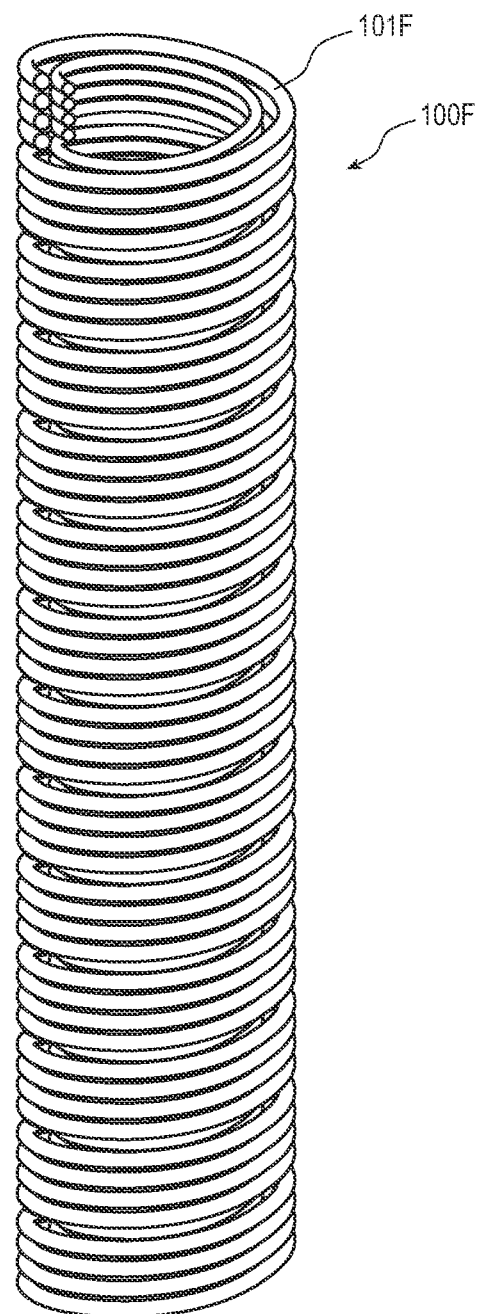
FIG. 3G illustrates yet another embodiment of a tubular scaffold.

FIG. 3F illustrates an embodiment of a tubular scaffold 100E comprised of four filaments 101E helically wound around a hollow core. FIG. 3G illustrates another embodiment of a tubular scaffold 100F comprising two layers of helically wound filaments 101F also with a hollow core. In some embodiments the filaments 101E, 101F of either embodiment may all be of the same material, or multiple materials may be used for filaments of either scaffold 100E, 100F.

Scaffolds within the scope of this disclosure may be comprised of a variety of materials. Any number of bioabsorbable materials including polymers, collagens, metals, ceramics, composites, glasses, plastics, nanoparticles, vegetables and vegetable oils, soaps, gels, and other materials, both natural and synthetic, are within the scope of this disclosure. Examples of polymers that are bioabsorbable and induce fibrosis include polyamides, esters, anhydrides, acetals, carbonates, amides, urethanes, and phosphates.

Other examples of biodegradable polymers or plastics include Polyhydroxyalkanoates (PHAs), poly-3-hydroxybutyrates (PHBs), polyhydroxyvalerates (PHVs), polyhydroxyhexanoates (PHHs), polylactic acid, starch blends or thermoplastic polymers, starch/polylactic acid, starch/polycaprolactone, starch/polybutylene-adipate-co-terephthalate, cellulose esters, cellulose acetate, nitrocellulose, biodegradable petroleum-based plastics, such as polyglycolic acid (PGA), polybutylene succinate (PBS), polypropylene, polycaprolactone, polyvinyl alcohol (PVA), polybutylene adipate terephthalate (PBAT), n-alkanes, branched alkanes, low molecular weight aromatics, cyclic alkanes, high molecular weight aromatics, polar polymers, lignins, biodegradable conducting polymers (CPs), carbon or noncarbon nanoparticles, oligomer-based biodegradables, hydrolyzed esters, hydrazones, polyparadioxanone (PPD), etc. Other bioabsorbable polymers in addition to these examples can be used.

As grouped by chemical families, additional bioabsorbable polymers within the scope of this disclosure include poly(ester urethanes), poly(anhydrides) (including poly(carboxy phenoxy propane-co-sebacic acid)), poly(orthoesters), poly(propylene fumarate), poly(pseudo amino acids), poly (ester amides), poly(alkyl cyanacrylates), poly(phosphazenes), poly(phosphoesters), and poly(α-esters).

Some examples of bioabsorbable metals within the scope of this disclosure include iron-based, zinc-based, and magnesium-based alloys, either coated or uncoated; pure metals; metal alloys; metal matrix composites; and metal ceramic composites. Other bioabsorbable metals in addition to these examples can be used.

Some examples of biodegradable ceramics within the scope of this disclosure include dicalcium-based phosphates, etc. Other bioabsorbable ceramics in addition to these examples can be used.

Natural materials including catgut (chromatised or non-chromatised) are likewise within the scope of this disclosure.

Treatment materials within the scope of this disclosure may comprise combinations of the example materials discussed above. For example, a polymeric suture could be coated or partially coated with metal, ceramic particles, or other particles to change the inflammatory response profile of the treatment material. For example, in some embodiments, gold may be disposed on a portion of a scaffold to increase an inflammatory response, barium may be disposed on a portion of a scaffold for radiopacity, and/or other particles and or nanoparticles may be disposed on a portion of a scaffold to affect other properties of the scaffold.

Various suture materials may be used to create scaffolds within the scope of this disclosure. For example, commercially available bioabsorbable suture materials may be used to create braided or woven scaffolds. Caprosyn™ (glycolide, caprolactone, trimethylene carbonate, and lactide) and Biosyn™ (glycolide and trimethylene carbonate, and dioxaneare) are two commercially available examples of such sutures, though any other bioabsorbable suture material is within the scope of this disclosure. Caprosyn™ and Biosyn™ are examples of materials with different bioabsorption rates; in some potential embodiments a braided or woven scaffold may comprise filaments of each material. Other commercially available bioabsorbable sutures within the scope of this disclosure include Maxon™ (copolymer of glycolicacid and trimethylene carbonate), Polysorb™ (glycolide and lactide), Velosorb™ (glycolide and lactide), and V-Loc™ (glycolide, dioxanone, and trimethylene carbonate or a copolymer of glycolic acid and trimethylene carbonate). These examples of suture materials may bioabsorb in as short a time as 40 days or as long a time as six months or more.

In addition to the rate of bioabsorption, suture or other filament materials may be utilized based on the time period over which the material loses its tensile strength. For example, a suture that fully bioabsorbs over 40 days may lose its tensile strength in as little as five days or less. Thus, materials may be utilized that continue to induce an inflammatory response as the material bioabsorbs, but the ability of the material to constrain or compress the body lumen may quickly dissipate.

Other suture materials within the scope of this disclosure include polypropylenes, poly L-lactide/glycolides, polyesters, polybutilates, silks, vicryls, coated vicryls, polygalactins, polydiaxonones, Monocryl, and Vicryl Rapide.

Suture materials used for scaffolds within the scope of this disclosure may be monofilament, braided, multistrand, coated, natural, synthetic, and so forth. Sutures of various sizes and diameters are within the scope of this disclosure. For example, in some embodiments sutures with a cross sectional diameter of between 0.001 mm and 1 mm, including between 0.001 mm and 0.800 mm are within the scope of this disclosure. Sutures within this size range correspond to sutures ranging from USP size 12-0 to 2-0 and from 0 to 5. Sutures or other filaments as used herein may include markings denoting length along the suture.

Scaffolds within the scope of this disclosure may also comprise permanent or nonbioabsorbable materials. For example, scaffolds within the scope of this disclosure may contain permanent filaments as well as bioabsorbable filaments. In some embodiments, the majority of scaffold may comprise bioabsorbable material while a smaller portion comprises permanent material. Embodiments of scaffolds wherein greater than 80%, greater than 90%, greater than 95%, and greater than 99% of the material of the scaffold (by weight or by volume) is bioabsorbable are within the scope of this disclosure. Embodiments wherein a single filament comprises a nonbioabsorbable material and embodiments wherein two, three, or four filaments of a scaffold are nonbioabsorbable are likewise within the scope of this disclosure.

Scaffolds of various sizes are within the scope of this disclosure. Tubular woven scaffolds (such as scaffolds 100A, 100B, and 100C of FIGS. 3A-3C) may range from 0.25 cm to 10 cm in diameter, including from 0.5 cm to 6 cm and from 2 cm to 4 cm and have a wall thickness between 0.05 mm to 10 mm, including from 0.05 mm to 5 mm and from 0.05 mm to 3 mm Flat woven scaffolds such as scaffold 100D of FIG. 3D may range from 0.5 cm to 10 cm in height, including from 0.5 cm to 6 cm and from 2 cm to 4 and from 0.05 mm to 10 mm in wall thickness, including from 0.05 mm to 5 mm and from 0.5 mm to 3 mm.

During use and treatment, scaffolds within the scope of this disclosure may be disposed around a body lumen adjacent a sphincter location. The scaffold may be wrapped around the body lumen a single time or wrapped around multiple times with or without overlapping wraps.

As also noted above, scaffolds within the scope of this disclosure may comprise a variety of materials. For example, a scaffold may be comprised of a plurality of filaments comprising a first material and a plurality of filaments comprising a second material. Scaffolds comprising three, four, five, or more materials are likewise within the scope of this disclosure. The different plurality of materials can be configured with different material properties such as strength, elasticity, rate of bioabsorption, thickness, surface finish, the presence or absence of barbs along the filament, and so forth. V-Loc™ sutures, also discussed above, are one example of a barbed suture.

While any combination of any number of materials disclosed herein are within the scope of this disclosure, as noted above, in some embodiments a scaffold may be comprised of two or more materials each with different bioabsorption rates. Such scaffolds may be configured to induce different amounts of inflammatory response at different time periods and/or sustain an inflammatory response over a certain time period. One such example is a scaffold comprised partially of Caprosyn™, which bioabsorbs completely in 40 to 50 days, and Biosyn™, which bioabsorbs in 90 to 110 days. In some embodiments two-thirds of the filaments of a scaffold may comprise Caprosyn™ and one-third Biosyn™, though any ratio of materials is within the scope of this disclosure. In another embodiment a scaffold may be comprised of two-thirds Caprosyn™ filaments and one-third V-Loc™ filaments. In another example, a scaffold may be partially of fully comprised of polydioxanone including embodiments wherein the polydioxanone is combined with polyethylene glycol and/or barium sulfate. Further embodiments wherein a scaffold is partially or fully comprised of polydioxanone combined with poly lactide cocaprolactonecotrimethylene carbonate and/or barium sulfate are likewise within the scope of this disclosure. In some instances, polydioxanone materials, or co-polymers of glycolic acid and lactic acid (e.g Vicryl Rapide) may bioabsorb in about 7-12 days.

Figure 4A:
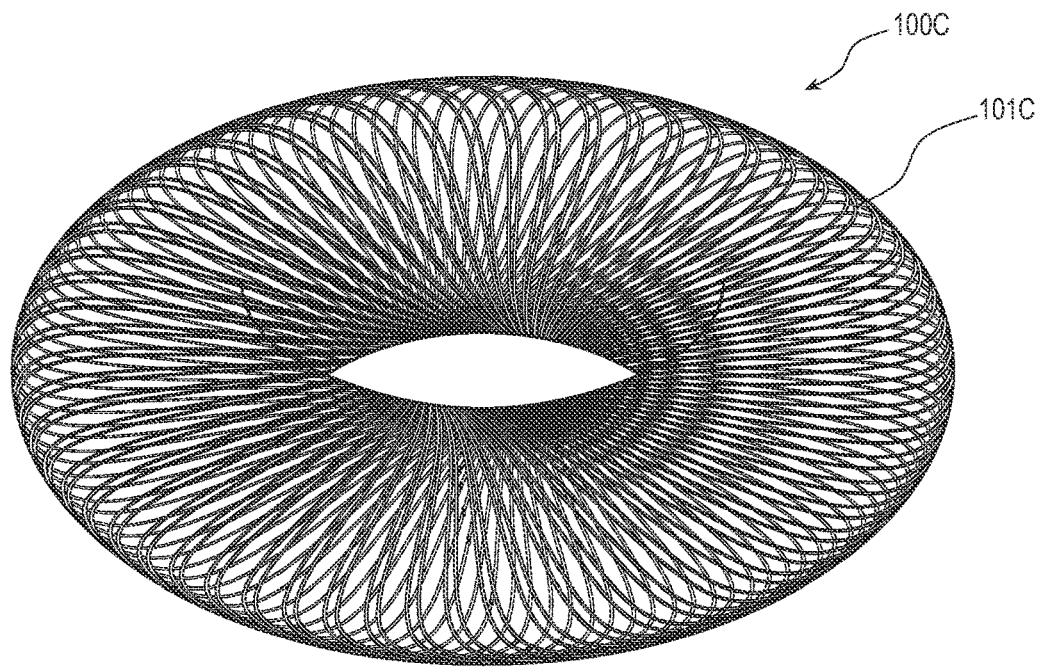
FIG. 4A illustrates the tubular scaffold of FIG. 3A disposed in a circumferential loop.

For example, FIG. 4A illustrates the tubular scaffold 100C of FIG. 3C disposed in a circumferential loop. To form a loop such as shown in FIG. 4A, a tubular scaffold (such as 100C) may be wrapped once around a body lumen and the two ends of the scaffold coupled together. Various methods of coupling the ends are within the scope of this disclosure, including tying the loose ends to each other with a knot, passing a suture around filaments 101C of both ends to stitch the ends together, coupling the ends with a fastener such a staple or clip, and so forth. The ends could also be sutured separately to structures within the body of the patient, such as the external wall of the lumen to be treated. Such a method could be utilized to join the ends of the scaffold and attach the scaffold to the body. Still further, in some tubular embodiments, one end of the device may be configured with a tapered nose cone configured to fit into the inside diameter of the opposite end to couple the ends together.

A flat woven scaffold such as scaffold 100D of FIG. 3D may also be disposed in a circumferential loop similar to the arrangement of scaffold 100C in FIG. 4A. As with a tubular scaffold, a flat woven scaffold such as 100D may be wrapped around the lumen to be treated and the two ends coupled to each other and/or to the lumen or other bodily structure. The ends could be tied together, stitched together with a suture that passes around the filaments 101D of the scaffold 100D, and/or coupled with a fastener such as a staple or clip. Analogous to the nose cone arrangement of a tubular scaffold as noted above, a flat woven scaffold such as 100D may be configured with tongue and groove features on opposite ends configured to couple to each other.

Figure 4B:
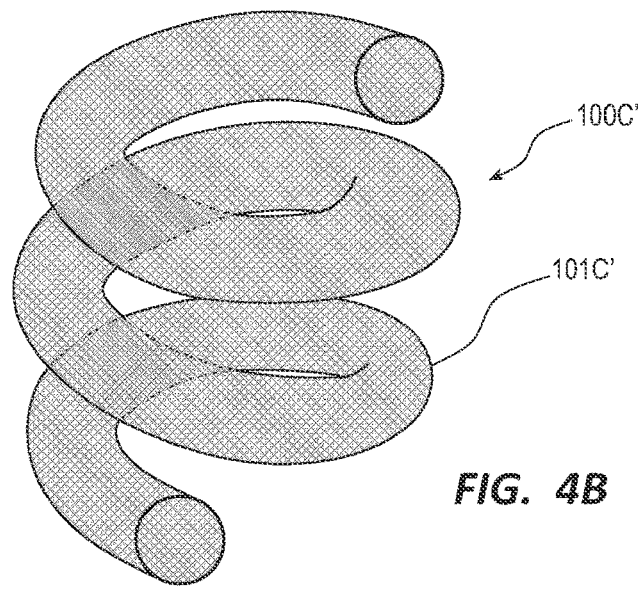
FIG. 4B illustrates a tubular scaffold disposed to define multiple helical loops.

Tubular, flat, and other scaffold shapes may be wrapped around the lumen to be treated multiple times. FIG. 4B illustrates a tubular scaffold 100C' disposed to define multiple helical loops. Any number of loops in such an arrangement are within the scope of this disclosure. When wrapped in non-overlapping loops, the ends of the scaffold 100C' may each be coupled to the lumen to be treated, for example by running a suture around filaments 101C' and stitching them to the surface of the lumen to be treated.

Figure 4C:
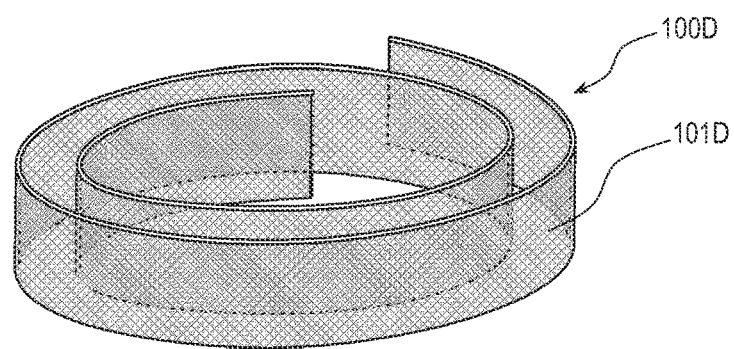
FIG. 4C illustrates the flat woven scaffold of FIG. 3D disposed in overlapping loops.
Figure 4D:
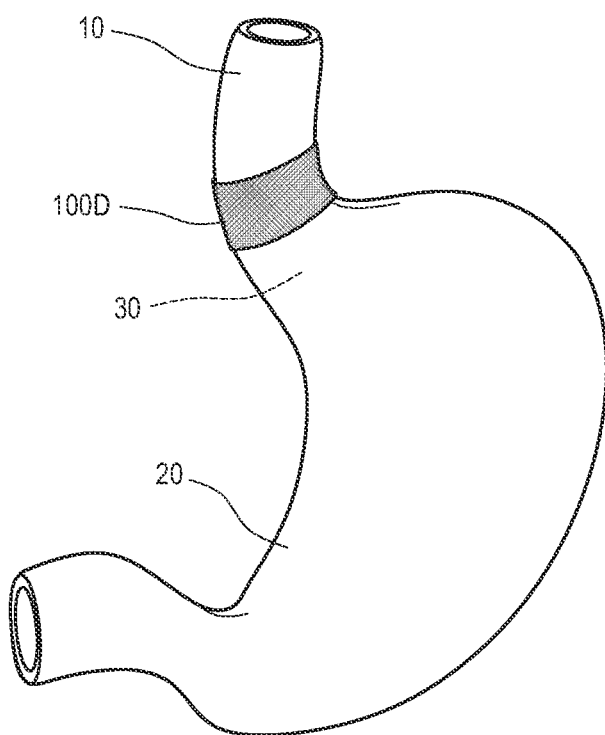
FIG. 4D illustrates the flat woven scaffold of FIG. 3D disposed around a portion of the esophagus, stomach, and LES.

Furthermore, tubular, flat, or other scaffold shapes, or combinations of tubular or flat shapes, may be wrapped around the lumen to be treated in overlapping loops. FIG. 4C illustrates the flat woven scaffold 100D of FIG. 3D disposed in overlapping loops. While the arrangement shown in FIG. 4C overlaps completely, arrangements where such loops partially overlap are within the scope of this disclosure as well. The ends of the scaffold 100D may be coupled to the lumen to be treated, for example by suturing the filaments 101D to the body lumen. FIG. 4D illustrates the flat woven scaffold 100D disposed around the esophagus 10 adjacent the LES 30 and the stomach 20. FIG. 4D illustrates an example of how the two ends of the flat woven scaffold 100D may be butted together and coupled (e.g., via a suture, a tongue and groove arrangement, or other coupling methods).

Figure 4E:
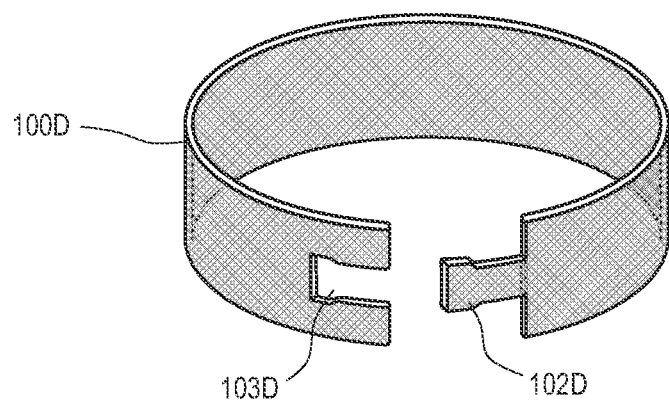
FIG. 4E illustrates the scaffold of FIG. 3D, shown with tongue and groove coupling features on opposite ends of the scaffold.

FIG. 4E illustrates one embodiment of a shape or structure for coupling the ends of scaffold together. FIG. 4E illustrates the scaffold 100D of FIG. 3D, shown with tongue 102D and groove 103D features on opposite ends of the scaffold 100D. The tongue 102D and groove 103D features can be configured to mate together to couple the ends of the scaffold 100D together. These features can be further coupled via a suture, clip, or other fastener. Embodiments wherein other portions of one end are configured to mate with the other are also within the scope of this disclosure, including embodiments where the tongue and groove portions are formed along the length of edges or at other points along the scaffold 100D. Though the tongue and groove design in shown with a flat scaffold, similar concepts can be applied to tubular scaffolds and scaffolds of other shapes. Tubular scaffolds wherein one end is configured to fit within the other end are also within the scope of this disclosure.

Additionally, scaffolds with different shapes or structures along the length of the scaffold are within the scope of this disclosure. For example, a scaffold may have a tubular cross section for a portion of its length and a flat woven structure along a different portion. Any shape or structure of scaffold can be used with any other. Embodiments where a scaffold is configured with a plurality of treatment sections coupled together by smaller linking elements (such as a single filament) may be utilized to create a non-continuous pattern of inflammation around a lumen. Stated another way, scaffolds within the scope of this disclosure may define a plurality of zones along the length of the scaffold wherein the filament density of the zones may or may not differ. Still further, scaffolds within the scope of this disclosure may define zones wherein any parameter, for example, cross sectional shape or structure, filament density, filament diameter, use of woven or continuous materials, number of materials comprising the zone, surface characteristics of the scaffold, and so forth may or may not vary between zones. Scaffolds may be circumferential, or configured to be disposed about the circumference of a sphincter (or tissue adjacent a sphincter), hemi-circumferential, partially circumferential, piecemeal, or other configurations. Braided scaffolds, non-woven scaffolds formed of filaments, scaffolds of porous materials, and so forth are within the scope of this disclosure. Filaments may be monofilament or may be comprised of twisted or braided sub-filaments.

Scaffolds within the scope of this disclosure may be implanted via surgical processes including laparoscopic procedures. In some embodiments, a practitioner may surgically implant the scaffold around the outside surface of an organ or lumen adjacent a sphincter location. As also noted above, a practitioner may wrap the scaffold around the organ or lumen any number of times, including one, two, three, four, five, or more wraps. (See FIG. 2E for an example of a scaffold 100' wrapped twice around the esophagus 10.) Such wraps may be longitudinally separated from each other (such that the scaffold helically winds along the lumen with spaces between the loops), helically wound such that adjacent loops touch but do not overlap, helically wound such that adjacent loops partially overlap, or wound such that the loops directly overlap. Any combination of these arrangements may be created along a treatment length of the organ and/or lumen (e.g., overlapping along a longitudinal portion and spaced along another longitudinal portion).

The scaffold may be wrapped around the organ or lumen such that portions of the scaffold extend beyond the sphincter to be treated. For example, when placing a scaffold around the esophagus adjacent the LES, the scaffold may be disposed around the region of the GEJ/LES, and extending one, two, three, four, or more centimeters along the esophagus and extending one, two, three, or more centimeters onto the proximal portion of the stomach. Thus, the scaffold may partially surround and extend beyond the LES.

As also noted above, during a procedure to implant a scaffold, a practitioner may dispose the scaffold around the body organ or lumen to be treated such that the scaffold contacts but does not compress the body organ or lumen. Additionally, it is within the scope of this disclosure to more loosely dispose the scaffold around the body organ or lumen such that there is slack on the scaffold as it extends around the organ or lumen or to dispose the scaffold more tightly such that it partially compresses a portion of the body organ or lumen. Scaffolds may be disposed around bodily tissue adjacent a sphincter without directly fixing the scaffold to the tissue, or scaffolds may be coupled to bodily tissue (for example via bioabsorbable sutures, permanent sutures, stapes, clips, and so forth). Scaffolds disposed adjacent a sphincter may be disposed in contact with tissue that surrounds the sphincter or may be disposed adjacent but not in contact with tissue surrounding the sphincter. In some embodiments a scaffold adjacent a sphincter may be disposed in contact with the sphincter, in contact with tissue (such as the wall of a body lumen or organ) that is in direct contact with the sphincter, and/or disposed such that there is a gap between the scaffold and the wall of a body lumen or organ containing the sphincter. Gaps between the external wall of a body lumen or organ containing a sphincter and a scaffold from 0 to 5 cm, 0 to 3 cm, and 0 to 1 cm are within the scope of this disclosure.

Methods of treatment within the scope of this disclosure include methods of inducing an inflammatory response and/or inducing the formation of a tissue collar around a body organ or lumen adjacent a sphincter location. In some instances, such treatments comprise surgically disposing a scaffold at or adjacent the organ or lumen to be treated. Methods wherein a scaffold is disposed completely around the body organ or lumen as well as methods wherein the scaffold is disposed only partially around the body organ or lumen are within the scope of this disclosure. For example, a scaffold may extend partially around the external wall of the organ or lumen and be sutured to the external wall of the organ or lumen at the ends of the scaffold. Embodiments wherein the scaffold extends 180 degrees around the organ or lumen and embodiments wherein the scaffold extends more or less than this are within the scope of this disclosure.

Furthermore, embodiments wherein the scaffold comprises wider treatment portions (such as braided or woven matrices of filaments) coupled together by narrower surface area coupling portions (such as a single suture or group of sutures with less surface area than the treatment portions) are within the scope of this disclosure. Thus, in some treatments a single scaffold may be applied to induce an inflammatory response and/or tissue collar along discontinuous segments around or along a lumen to be treated. Embodiments where discrete portions of a scaffolding material are coupled to the lumen as patches to induce areas of inflammation are likewise within the scope of this disclosure.

Treatments within the scope of this disclosure may be performed via open surgery; laparoscopic surgery; endoscopic surgery; fluoroscopic surgery; needle access, including guided needle access; radiologically, via peroral endoscopic myotomy (POEM), and so forth. In some embodiments, a scaffold may be implanted around the organ or lumen to be treated, while in other embodiments the scaffold may be implanted into the tissue of the organ or lumen to be treated. For example, a scaffold or portion of a scaffold may be inserted into a portion of the wall of an organ or lumen to be treated. Such procedures may be done through endoscopy or endoscopic surgery entering the wall of the lumen from the inside of the lumen or injecting material endoscopically via the inside of a lumen or radiologically via extrinsic injection via a needle. These injections can be done piecemeal, circumferentially, hemi-circumferentially into the wall of the organ or adjacent to the wall, including injections adjacent but external to the wall. Procedures where biodegradable materials are disposed directly against the tissue of a sphincter (for example via an endoscopic or radiologic procedure) to induce inflammation of the sphincter are likewise within the scope of this disclosure. Biodegradable material can be placed externally via accessing the wall internally, via endoscopy for example, penetrating the wall from the inside out with an endoscopic needle for example, extending the needle through the wall and depositing material external or adjacent to the wall. The external portion of the organ adjacent to the sphincter can also be directly reached by percutaneous penetration of a needle via radiologic guidance for example, to the external aspect of the organ adjacent to the sphincter, and depositing of material via needle injection for example.

Figure 5A:
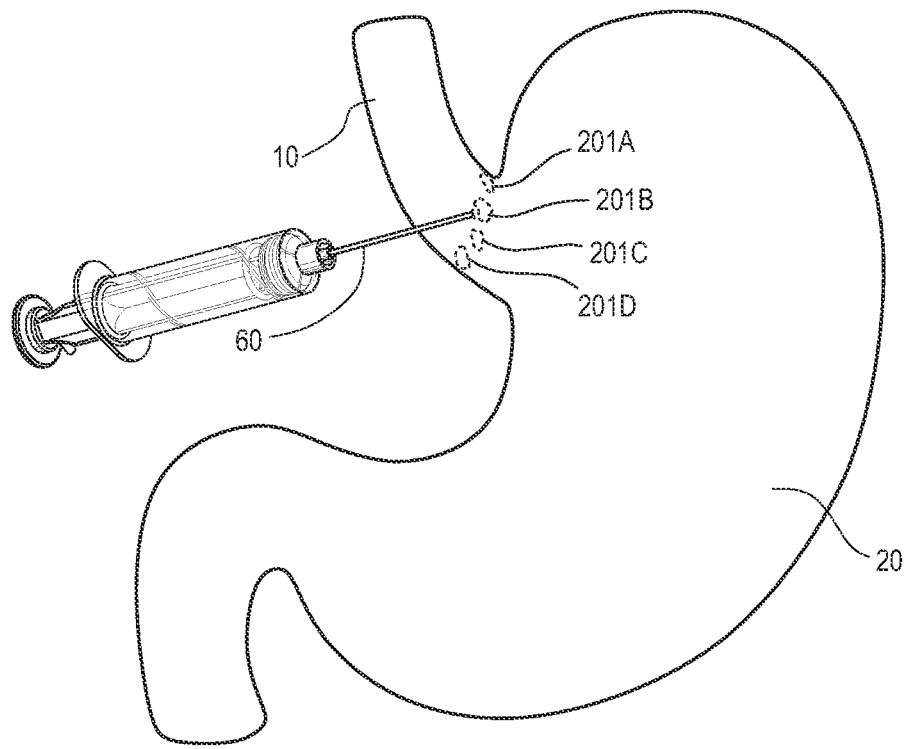
FIG. 5A illustrates a portion of an esophagus, stomach, and LES with a needle for introducing bioabsorbable material.

For example, FIG. 5A illustrates a portion of the esophagus 10 and the stomach 20 with a percutaneous needle 60 for introducing bioabsorbable material 201A, 201B, 201C, 201D adjacent to the external wall of the esophagus 10. During some treatments, a bioabsorbable material may be injected via a needle into the wall of an organ or lumen to be treated. The bioabsorbable material 201A, 201B, 201C, 201D could also be injected directly into the mucosa and/or submucosa, muscle layers, adventitia, and so forth of the esophagus 10 in some treatments.

The bioabsorbable material 201A, 201B, 201C, 201D may be injected as a continuous band, and injected in discrete segments or portions around the circumference of the lumen to be treated, such as the esophagus 10. The bioabsorbable material 201A, 201B, 201C, 201D can extend longitudinally along a length of the organ or lumen to be treated and may extend beyond the sphincter location at either longitudinal end.

Injections of materials into the wall of the esophagus, or into the wall of another body organ or lumen adjacent a sphincter, or external to a sphincter, may be performed percutaneously, endoscopically, radiologically, laparoscopically, fluoroscopically, via POEM, and so forth.

Figure 5B:
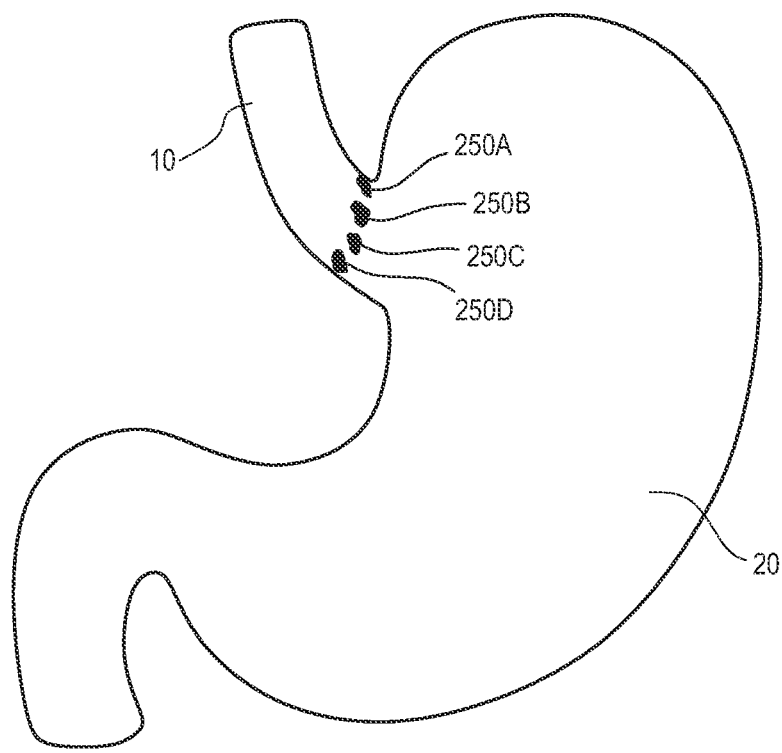
FIG. 5B illustrates the portion of the esophagus, stomach, and LES of FIG. 5A showing tissue growth in response to the material of FIG. 5A after bioabsorption of the material.

As the bioabsorbable material 201A, 201B, 201C, 201D breaks down in the body, an inflammatory response may lead to the formation of fibrosis, collagen, and/or scar tissue. FIG. 5B illustrates the portion of the esophagus 10 and the stomach 20 of FIG. 5A showing tissue growth in response to the bioabsorbable material 201A, 201B, 201C, 201D of FIG. 5A. Thus, tissue collars 250A, 250B, 250C, 250D may be disposed externally around the esophagus 10 in any pattern as discussed above or directly into the wall of esophagus 10 in any pattern as discussed above. Any number of treatment sites and locations are within the scope of this disclosure.

The bioabsorbable material 201A, 201B, 201C, 201D injected or placed external to, or in the wall of the lumen may comprise a liquid, gel, suspension, plugs or pledgets of solid materials, and so forth. As compared to injection of permanent materials into the wall of a lumen, use of bioabsorbable materials reduces or eliminates issues related to infection, or migration of the permanent material to other areas of the body.

Figure 6A:
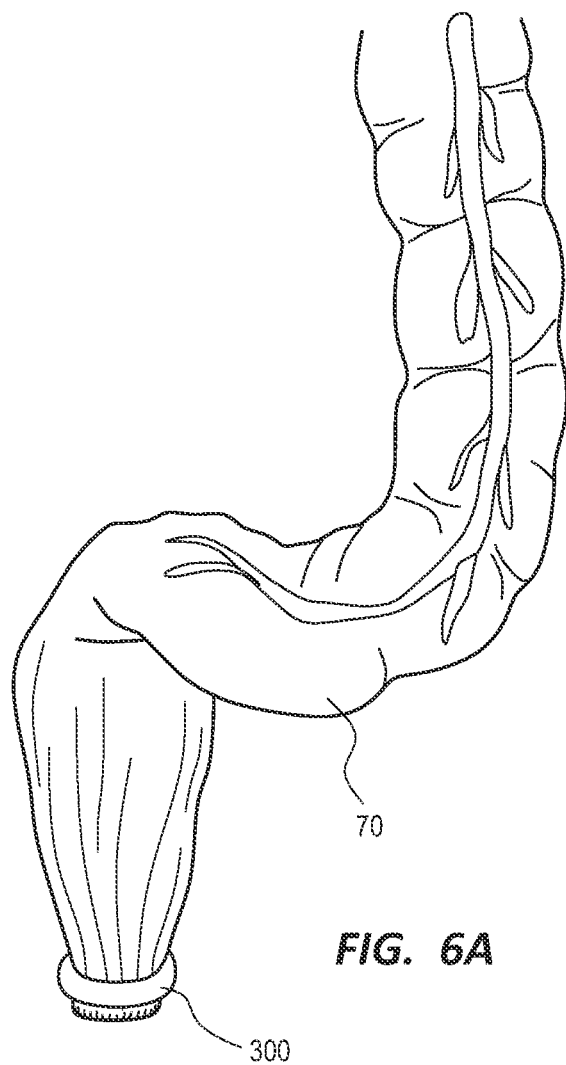
FIG. 6A illustrates a portion of a colon, rectum, and anal sphincter with a biodegradable scaffold shown around the anal sphincter.
Figure 6B:
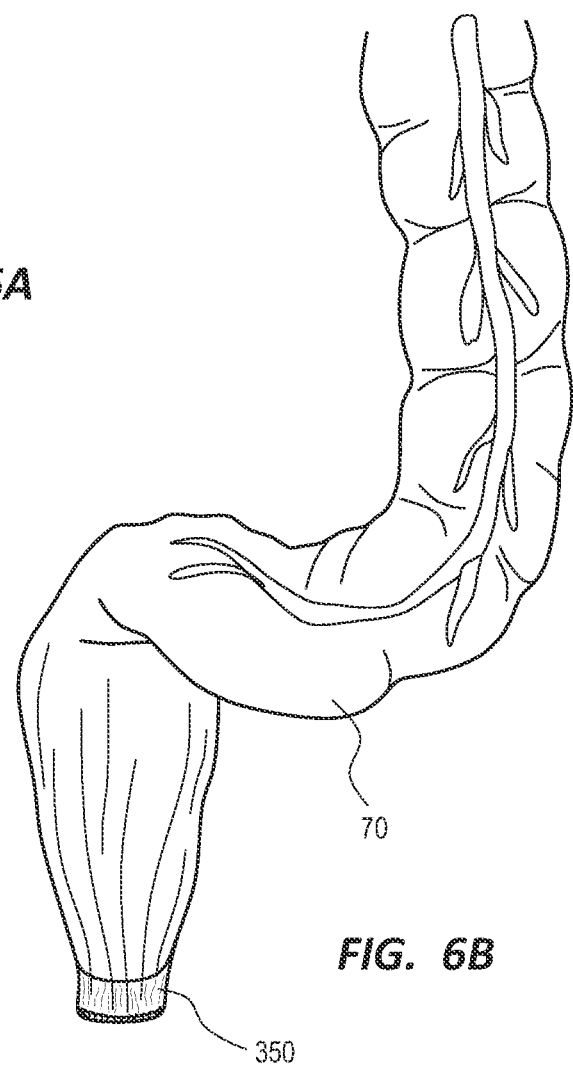
FIG. 6B illustrates a portion of the colon, rectum, and anal sphincter of FIG. 6A with a tissue collar shown around the sphincter after bioabsorption of the scaffold.
Figure 6C:
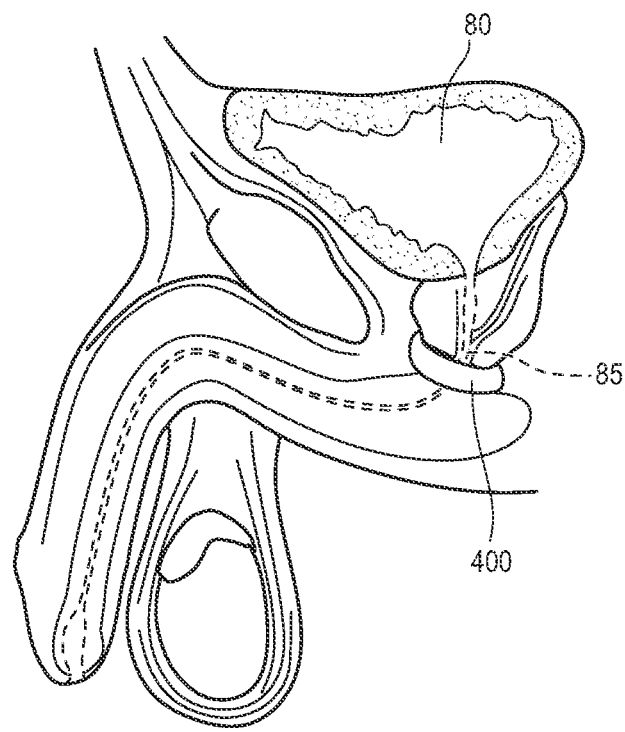
FIG. 6C illustrates a portion of a bladder, urethra, and urethral sphincter with a biodegradable scaffold shown around the urethral sphincter.
Figure 6D:
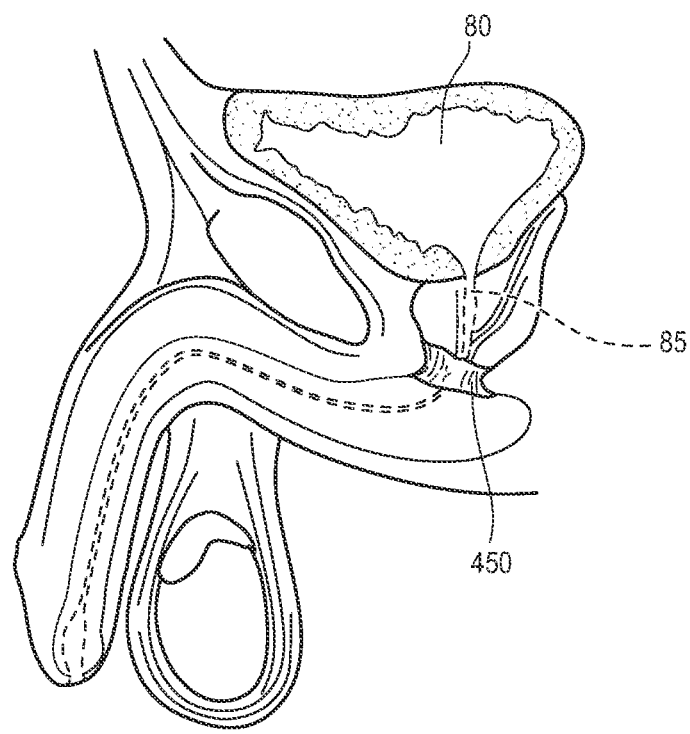
FIG. 6D illustrates a portion of the bladder, urethra, and urinary sphincter of FIG. 6C with a tissue collar shown around the urethral sphincter after bioabsorption of the scaffold.

As noted above, the devices, concepts, and procedures disclosed herein may be configured to treat a variety of sphincters in a variety of body lumens. As discussed above, though this disclosure may be applied to treat the LES and GERD, the application of this disclosure is not limited to such treatments. FIGS. 6A-6D illustrate examples of additional treatment locations. These examples are not meant to constitute a complete list of treatment locations; rather, they are meant as additional examples of treatments within the scope of this disclosure. FIG. 6A illustrates a portion of a colon 70 with a scaffold 300 shown around the anal sphincter. FIG. 6B illustrates a portion of the colon 70 with a tissue collar 350 shown around the anal sphincter area of the rectum and anus. FIG. 6C illustrates a portion of a bladder 80 and urethra 82 with a scaffold 400 shown around the urinary sphincter of the urethra. FIG. 6D illustrates a portion of the bladder 80 with a tissue collar 450 shown around the urinary sphincter of the urethra 82. Analogous to the discussion of the LES and GERD above, an inflammatory response may be induced adjacent the anal or urinary sphincter to reinforce the sphincter and treat disorders of the sphincter. Thus, the devices and methods disclosed herein may be configured for treatment of a variety of conditions (including fecal and urinary incontinence as well as other disorders of these or other sphincters) in an analogous manner to treatment of the LES for GERD. Additional applications include, but are not limed to, analogous cardiac, neurological, renal, and orthopedic treatments. For example, treatments may be used to reinforce a cardiac valve, an aneurysm, bones, ligaments, tendons, or other portions of the body.

It is noted that this disclosure recites certain features and applications in connection with certain drawings or examples of treatments for conciseness and clarity, though such disclosure may be applied to other figures and examples throughout the disclosure. In the figures, like features are designated with like reference numerals, with the leading digits incremented, letters added following the digits, and/or the addition of prime "'" markers. For example, the embodiment depicted in FIGS. 2A-2D includes a scaffold 100 that may, in some respects, resemble the scaffolds 100A, 100B, 100C, 100D, 100C' of FIGS. 3A-4C and the embodiment depicted in FIGS. 2A-2D includes a tissue collar 150 that may resemble the tissue collars 250A, 250B, 250C, 250D, 350, 450 of FIGS. 5B-6B. Relevant disclosure set forth above regarding similarly identified features thus may not be repeated for each embodiment. Moreover, specific features and related components shown in some embodiments may not be shown or identified by a reference numeral in the drawings or specifically discussed in connection with each embodiment. However, such features may clearly be the same, or substantially the same, as features depicted in other embodiments and/or described with respect to such embodiments. Accordingly, the relevant descriptions of such features apply equally to the features of each embodiment. Any suitable combination of the features, and variations of the same, described with respect one embodiment can be employed with the components of the other embodiments, and vice versa.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art and the benefit of this disclosure, that changes may be made to the details of the above-described embodiments without departing from the underlying principles of the present disclosure.

Example of a Biodegradable Scaffold for the Treatment of GERD

In one example, a Caprosyn™ monofilament size 1 material was used to construct a scaffold that was implanted in a porcine model as a treatment for GERD as described below. Specifically, a scaffold was created that was comprised of 0.020" diameter Caprosyn monofilament in a braided configuration with 8 filaments. The tubular braided scaffold had an inner diameter of 0.125" and between 10-20 picks per inch.

Prototype Testing

The hollow Caprosyn™ braided suture was then implanted 360 degrees around the esophagus of a Yorkshire swine in the region of the GEJ/LES below the diaphragm. The implant was sutured to the esophagus wall in three spots with Prolene to secure it in place.

The animal was survived for 12 weeks post implant for follow up testing and histology.

Follow Up Studies

Dysphagia Test

The animal survived 12 weeks and showed no signs of dysphagia, being able to maintain appetite, eat consistently and swallow food without difficulty. A barium swallow test was conducted to ensure that there was no stenosis or stricture in the region of the lower esophageal sphincter (LES). Several swallows were viewed with fluoroscopic imaging and no dysphagia was observed.

LES Yield Pressure (Force Required to Open the LES from the Gastric Aspect)

A custom balloon catheter was used to measure the LES yield pressure (LES opening force) prior to the implant, directly after implant and at 12-week follow up. The custom balloon catheter was inserted into the empty stomach of the animal, filled with 15 cc of fluid and connected to a pressure sensor. The balloon was gradually pulled from the stomach through the LES and into the esophagus recording the pressure through the transition. The results of the balloon pull-through test are in table 1 below.

TABLE 1

| Time Point | Baseline (mmHg) Pre-Pull Through | Peak Value (mmHg) | Delta in Pressure (mmHg) | Percent Increase/ Decrease from Baseline |
|---|---|---|---|---|
| Pre-Implant - Open Abdomen | 26.9 | 164.7 | 137.8 | 0 |
| Post Implant - Immediately - Open Abdomen | 32.0 | 194.3 | 162.3 | 18% |
| Post Implant - 12 weeks - Closed Abdomen | 53.2 | 201.9 | 148.7 | 8% |
| Post Implant - 12 weeks - Open Abdomen | 43.3 | 249.1 | 205.8 | 49% |

As seen from the LES yield pressure results, immediately after implant the LES yield pressure was increased by approximately 18%. Additionally, 12-week follow up testing showed similar results with an increase of approximately 49% which is likely due to the collagen band induced by the bioabsorbable suture augmenting the LES.

Scar Formation/Pathology

The esophagus, LES and stomach were explanted post testing for further analysis of fibrosis/collagen band location and thickness. Initial observations illustrated a collagen band ⅔ of the way around the circumference of the esophagus directly in-line with the Prolene securement sutures used at implant and directly below the diaphragm.

Macroscopic observations: The serosal surface of the stomach surrounding the gastroesophageal junction exhibited semi-firm to firm red to tan adhesions, comprising ~15-20% of the gastric serosa. Fibrosis expanded the cardia serosa pars oesophagea and there were no other abnormalities noted.

Microscopic observations: The serosal surfaces of the esophagus and stomach within the tissue sections were minimally to moderately expanded by irregular and papilliform streams of fibrosis.

Observations

The initial feasibility prototypes demonstrated that a braid of Caprosyn™ monofilament suture can be heat set it to create a stable hollow braided suture implant. The implant itself has shape memory allowing the braid to stretch as food is ingested through the esophagus and rebounds to augment the sphincter post swallowing. The hollow suture was easy to slide around the esophagus and was easy to suture in place. Analysis of the LES yield pressure (LES opening force) demonstrated that at baseline/pre-implant, the pressure increase during the balloon LES pull-through was 137.8 mmHg. Immediately post-implant, the pressure measurement was 162.3 mmHg resulting in an ~18% increase in LES yield pressure (opening force), demonstrating LES augmentation which should help reduce/prevent GERD. The animal survived the implant and abdominal closure. There was no sign of dysphagia during the 12-week survival as well as during fluoroscopic imaging of the barium sulfate swallow. The pressure measurement for the LES balloon pull through test at the 12-week follow up was 205.8 mmHG resulting in a 49% increase from pre-implant. The explant of the esophagus illustrated collagen/fibrosis formation in the region of the completely absorbed implant.

Based on these results, initial feasibility testing was remarkably successful. A braided bioabsorbable suture with shape memory was produced and implanted around the esophagus, increasing the LES yield pressure immediately, without causing dysphagia. Additionally, the device induced a fibrotic response/collagen band that increased the LES yield pressure and decreased GEJ compliance on a chronic basis, once the implant was fully absorbed.

We claim:

1. A bioabsorbable scaffold, comprising:
a matrix comprising:
a first bioabsorbable filament; and
a second bioabsorbable filament,
wherein the matrix is configured to be disposed at least partially around a body portion or a sphincter of a patient,
wherein the matrix is configured to induce a formation of collagen tissue about a portion of the sphincter,
wherein the first bioabsorbable filament has a first bioabsorption rate and the second bioabsorbable filament has a second bioabsorption rate that is different from the first bioabsorption rate, and
wherein the matrix is configured to couple the body portion or the sphincter of the patient to an adjacent body portion.

2. The bioabsorbable scaffold of claim 1, wherein the second bioabsorbable filament is wound about the first bioabsorbable filament.

3. The bioabsorbable scaffold of claim 2, wherein the first bioabsorbable filament comprises a shape selected from the group consisting of a cylindrical shape, a hollow tubular shape, and combinations thereof.

4. The bioabsorbable scaffold of claim 1, wherein the first bioabsorbable filament and the second bioabsorbable filament are woven together.

5. The bioabsorbable scaffold of claim 4, wherein the matrix comprises a shape selected from the group consisting of a cylindrical shape, a hollow tubular shape, and combinations thereof.

6. The bioabsorbable scaffold of claim 4, wherein the matrix comprises a flat woven shape.

7. The bioabsorbable scaffold of claim 1, wherein the matrix consists of 100% bioabsorbable material.

8. The bioabsorbable scaffold of claim 1, wherein the matrix further comprises a third bioabsorbable filament having a third bioabsorption rate that is different from each of the first bioabsorption rate and the second bioabsorption rate.

9. A bioabsorbable scaffold, comprising:
a matrix comprising:
a first end;
a second end opposite the first end; and
a bioabsorbable filament extending from the first end to the second end,
wherein the matrix is configured to be disposed at least partially around a body portion or a sphincter of a patient,
wherein the matrix is configured to induce a formation of collagen tissue about a portion of the sphincter,
wherein the first end and the second end remain in non-touching relation to one another, and
wherein the matrix is configured to couple the body portion or the sphincter of the patient to an adjacent body portion.

10. The bioabsorbable scaffold of claim 9, wherein the matrix is configured to be disposed around portions of the sphincter in a manner selected from the group consisting of partially circumferentially, a piecemeal fashion, and combinations thereof.

11. The bioabsorbable scaffold of claim 9, wherein the matrix is configured to be disposed fully circumferentially around the sphincter.

12. The bioabsorbable scaffold of claim 9, wherein the matrix is configured to expand in response to a natural expansion of the sphincter.

13. The bioabsorbable scaffold of claim 9, wherein the bioabsorbable filament comprises a constant filament density along a length of the matrix.

14. A bioabsorbable scaffold, comprising:
a matrix comprising a bioabsorbable filament,
wherein the matrix is configured to be disposed at least partially around a body portion or a sphincter of a patient,
wherein the matrix is configured to induce a formation of collagen tissue about a portion of the sphincter,
wherein the matrix is configured to be disposed helically about the sphincter, and
wherein the matrix is configured to couple the body portion or the sphincter of the patient to an adjacent body portion.

15. The bioabsorbable scaffold of claim 14, wherein the matrix comprises a first matrix, the bioabsorbable scaffold further comprising:
  a second matrix comprising a bioabsorbable filament,
  wherein the second matrix is configured to be disposed on or adjacent to the body portion or the sphincter of the patient, and
  wherein the second matrix is configured to be disposed helically about the sphincter.

16. The bioabsorbable scaffold of claim 15, wherein the second matrix is disposed concentrically within the first matrix.

17. The bioabsorbable scaffold of claim 15, wherein the first matrix and the second matrix are stacked with respect to one another.

18. The bioabsorbable scaffold of claim 14, wherein the matrix is configured to be disposed about the sphincter in a non-overlapping manner.

19. The bioabsorbable scaffold of claim 14, wherein the matrix is configured to be disposed about the sphincter in an overlapping manner.

20. The bioabsorbable scaffold of claim 14, wherein the matrix is configured to be completely absorbed into the body portion or the sphincter of the patient.

* * * * *